(12) United States Patent
Eidenberger

(10) Patent No.: US 9,849,178 B2
(45) Date of Patent: Dec. 26, 2017

(54) COMBINATION OF CAROTENOIDS AND EPI-LUTEIN

(71) Applicant: Gupron GmbH, Wels (AT)

(72) Inventor: Thomas Eidenberger, Steyr (AT)

(73) Assignee: GUPRON GMBH, Wels (AT)

( * ) Notice: Subject to any disclaimer, the term of this patent is extended or adjusted under 35 U.S.C. 154(b) by 284 days.

(21) Appl. No.: 13/896,148

(22) Filed: May 16, 2013

(65) Prior Publication Data

US 2013/0253070 A1   Sep. 26, 2013

Related U.S. Application Data

(62) Division of application No. 12/962,720, filed on Dec. 8, 2010, now abandoned.

(60) Provisional application No. 61/286,054, filed on Dec. 14, 2009.

(51) Int. Cl.
| | | |
|---|---|---|
| A61K 47/10 | (2017.01) | |
| A01N 43/20 | (2006.01) | |
| A61K 31/335 | (2006.01) | |
| A01N 43/24 | (2006.01) | |
| A61K 31/015 | (2006.01) | |
| A61K 31/055 | (2006.01) | |
| A61K 31/122 | (2006.01) | |
| A61K 45/06 | (2006.01) | |
| A61K 31/047 | (2006.01) | |

(52) U.S. Cl.
CPC ............ *A61K 47/10* (2013.01); *A61K 31/015* (2013.01); *A61K 31/047* (2013.01); *A61K 31/055* (2013.01); *A61K 31/122* (2013.01); *A61K 45/06* (2013.01)

(58) Field of Classification Search
CPC ....... A01N 43/20; A01N 43/24; A61K 31/335
USPC ....................................................... 514/475
See application file for complete search history.

(56) References Cited

U.S. PATENT DOCUMENTS

| | | |
|---|---|---|
| 6,420,614 B1 | 7/2002 | Eugster et al. |
| 6,818,798 B1 | 11/2004 | Khachik |
| 2004/0087664 A1* | 5/2004 | Marcus et al. ................ 514/691 |

FOREIGN PATENT DOCUMENTS

WO       WO 01/83414       11/2001

OTHER PUBLICATIONS

Norman et al. (Carotenoids in Health and Disease, 2004, p. 262).*
Khachik et al. ("The effect of lutein and zeaxanthin supplementation on metabolites of these carotenoids in the serum of persons aged 60 or older." Investigative Ophthalmology and Visual Science 47.12 (2006): 5234).*
Toyoda et al. ("Effect of dietary zeaxanthin on tissue distribution of zeaxanthin and lutein in quail." Investigative Ophthalmology and Visual Science 43.4 (2002): 1210-1221).*
PCT/EP2010/069659 International Search Report, dated Apr. 5, 2011 (4 pgs.).
Bucheker R. et al., "Search for the presence in egg yolk, in flowers of Caltha palustris and in autumn leave of 3'-epilutein(=(3R,3'S,6'R)-[beta],[epsilon]-carotene-3,3'-diol) and 3', O-didehyrolutein (=(3R,6'R)-3-hydroxy-[beta],[epsilon]-carotene-3'-one", Helvetica ChimcaActa 1979 CH, vol. 62, 8, 1979, pp. 2817-2824.
Carpentier Shannon et al., "Associations between lutein, zeaxanthin, and age-related macular degeneration: an overview", Critical reviews in food science and nutrition Apr. 2009, vol. 49, No. 4, Apr. 2009, pp. 313-326.
Khachik F. et al., "Transformations of selected carotenoids in plasma, liver, and ocular tissues of humans and in nonprimate anmimal models", Investigative opthalmology and visual science 20211 US, vol. 43, No. 11, Nov. 2002, pp. 3383-3392.

* cited by examiner

*Primary Examiner* — Layla Soroush
(74) *Attorney, Agent, or Firm* — Michael Ye; Andrews Kurth Kenyon LLP

(57) ABSTRACT

The invention describes the preparation and use of carotenoid and epi-lutein compositions to treat various ocular diseases.

8 Claims, 6 Drawing Sheets

COMBINATION OF CAROTENOIDS AND EPI-LUTEIN

CROSS REFERENCE TO RELATED APPLICATION(S)

This application is a divisional of U.S. patent application Ser. No. 12/962,720, filed Dec. 8, 2010, which claims priority to U.S. Provisional Patent Application No. 61/286,054, filed Dec. 14, 2009. The disclosures of which are incorporated by reference herein in their entirety.

FIELD OF THE INVENTION

The invention relates generally to combinations of epi-lutein with carotenoids, such as of lutein, zeaxanthin and related compositions.

BACKGROUND OF THE INVENTION

Carotenoids are yellow, red and orange pigments that are widely distributed in nature. Although specific carotenoids have been identified in various fruits and vegetables, bird feathers, egg-yolk, poultry skin, crustaceans and macular eye region, they are especially abundant in marigold petals, corn and leafy vegetables. The correlation between dietary carotenoids and carotenoids found in human serum and plasma indicate that only selected groups of carotenoids make their way into the human blood stream to exert their effect.

Carotenoids absorb light in the 400-500 nm region of the visible spectrum. This physical characteristic imparts the yellow/red color to the pigments. Carotenoids contain a conjugated backbone composed of isoprene units, which are usually inverted at the center of the molecule, imparting symmetry. Changes in geometrical configuration about the double bonds result in the existence of many cis- and trans-isomers. Mammalian species do not synthesize carotenoids and therefore these have to be obtained from dietary sources such as fruits, vegetables and egg yolks. In the recent years, carotenoids have been attributed several health benefits, which include prevention and or protection against serious health disorders.

Carotenoids are non-polar compounds classified into two sub-classes, namely more polar compounds called xanthophylls or oxy-carotenoids and non-polar hydrocarbon carotenes like [beta]-carotene, lycopene, etc. Both the sub-classes have at least nine conjugated double bonds responsible for the characteristic color of the carotenoids. Xanthophylls have ring structures at the end of the conjugated double bond chain with polar functionalities, such as hydroxyl or keto groups. Examples of xanthophylls include lutein, zeaxanthin, capsanthin, canthaxanthin, β-cryptoxanthin, astaxanthin, etc. As natural colorants and also for their role in human health, xanthophylls containing lutein and zeaxanthin have attracted the renewed attention of scientists and researchers in the biomedical, chemical and nutritional field in recent years.

Lutein and zeaxanthin contribute to yellow and orange-yellow color respectively. Lutein and zeaxanthin can be present in plant material in free form (non-esterified) and also as esters. Lutein is present in green leafy vegetables like spinach, kale and broccoli in the free form while fruits like mango, orange, papaya, red paprika, algae and yellow corn. These sources generally contain lutein in the form of its esters etc. Lutein is also present in the blood stream and various tissues in human body and particularly the macula, lens and retina of the eye.

Essentially, lutein esters and lutein in the free form are commercially important nutraceuticals obtained from marigold flowers. In the fresh marigold flowers, lutein esters exist in trans-isomeric form, whereas exposure to heat, light, oxygen, acid, etc. catalyses isomerization from trans- to cis-lutein geometric isomeric forms. As a nutraceutical and trod additive, the trans-isomeric form of lutein is preferred because of better bio-availability and deeper yellow color compared to the corresponding cis-isomeric form.

Various carotenoids are present in human plasma, but only the xanthophylls lutein and zeaxanthin are found in the retina in considerable amount, with particularly high levels in the macula lutea, the yellow spot in the center of the fovea. Degeneration of the retina and retinal pigment epithelium in the region of the macula lutea leads to eye diseases, such as age-related macular degeneration (AMD). Lutein and zeaxanthin are the predominant carotenoids in the human macula lutea. Epidemiological data suggest that an increased intake of diet enriched in lutein can diminish the risk of MAD and associated or related diseases.

Therefore, a need exists for the increased uptake of xanthophylls such as lutein and/or zeaxanthin in human plasma, and especially in the macula lutea.

BRIEF SUMMARY OF THE INVENTION

The present invention provides a composition including carotenoids and epi-lutein and methods to increase bioavailability of carotenoids in vivo.

The present invention also provides the use of the above composition in foods, beverages, and nutraceuticals.

The present invention further provides methods to prevent/treat/improve eye disorders/conditions/diseases, such as age related macular degeneration (AMD), development of cataracts, macular degeneration, pinguecula, etc.

With the epi-lutein combinations described herein, higher bioavailability can be achieved than with an equal amount of carotenoids than without epi-lutein. Based on experimental data, it is considered that the presence of epi-lutein in the presence of a carotenoid can enhance plasma concentration of the carotenoid.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
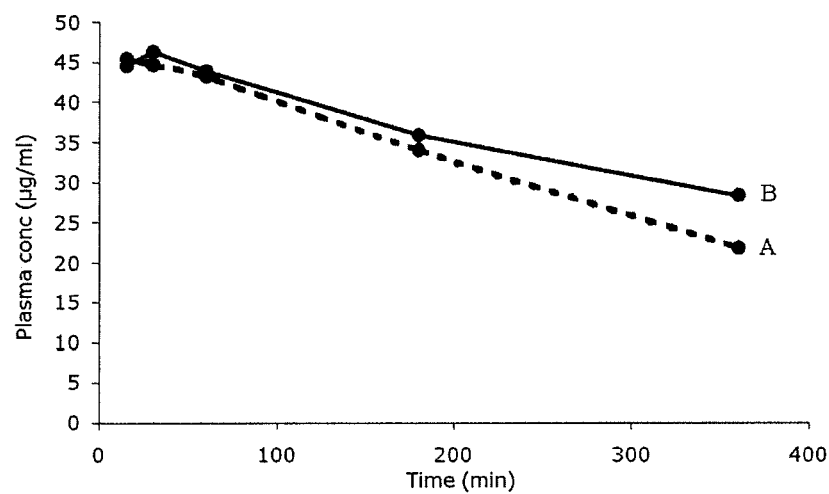
FIG. 1 shows the degradation of lutein with/without epi-lutein.

The present invention relates to the combinations of carotenoids, such as lutein and/or zeaxanthin with epi-lutein. It has been surprisingly found that epi-lutein has an effect on the uptake and retention of the carotenoid(s) in blood plasma. Subsequently, the carotenoids are more bioavailable for delivery to macula tissue.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Carotenoids are a class of hydrocarbons (carotenes) and the corresponding oxygenated derivatives are xanthophylls. They consist of eight isoprenoid units joined in such a manner that the arrangement of isoprenoid units is reversed at the center of the molecule so that the two central methyl groups are in a 1,6-position relationship and the remaining nonterminal methyl groups are in a 1,5-position relationship. All carotenoids may be formally derived from the acyclic $C_{40}H_{56}$ structure (1) (Compound I), having a long central chain of conjugated double bonds, by (f) hydrogenation, (2) dehydrogenation, (3) cyclization, or (4) oxidation, or any combination of these processes. The class also includes compounds that arise from certain rearrangements or degradations of the carbon skeleton (I) (lycopene), provided hat the two central methyl groups are retained.

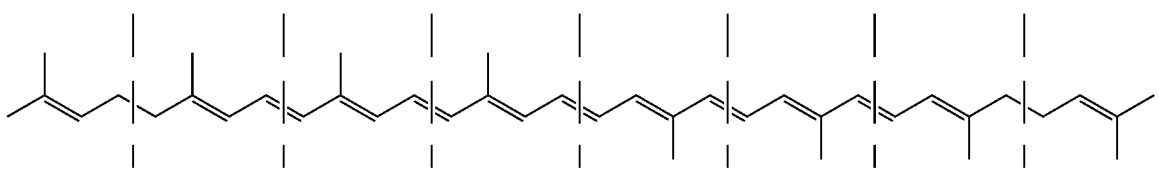

I

About 600 carotenoids have been isolated from natural sources. These carotenoids have been listed with their trivial and semisystematic names in Key to Carotenoids (Pfander, 1987) and in the Appendix of Carotenoids, Volume 1A (Kull & Pfander 1995) which also includes literature references for their spectroscopic and other properties. The structure is still uncertain for many of the carotenoids, including stereochemical assignments. In the cases where the structure is uncertain, resolution, followed by structural elucidation with modern spectroscopic methods (including high resolution nuclear magnetic resonance (NMR) spectroscopy) is necessary. About 370 of the naturally occurring carotenoids are chiral, bearing from one to five asymmetric carbon atoms, and in most cases one carotenoid occurs only in one configuration in Nature.

All specific names of cartenoids are based on the stem name carotene, which corresponds to the structure and numbering as in Compound II (carotene).

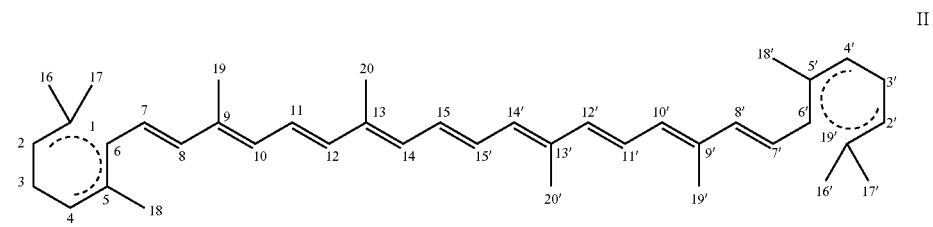 [SMILES: CC(/C=C/C=C(C)/C=C/CC(C)CCCC(C)C)=C\C=C\C=C(C)\C=C\C=C(C)\C=C\CC(C)CCCC(C)C]

II

The name of a specific compound is constructed by adding two Greek letters as prefixes (Compound fragments III) to the stem name carotene. The Greek letter prefixes are cited in alphabetical order noted in compounds IIa.

IIa

ψ 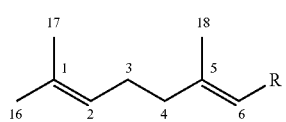

β 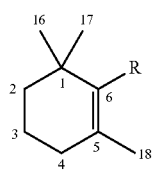

ε 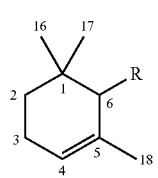

γ 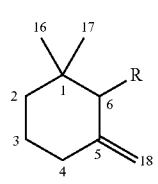

κ 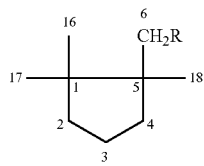

φ 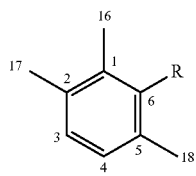

χ 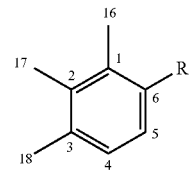

R = 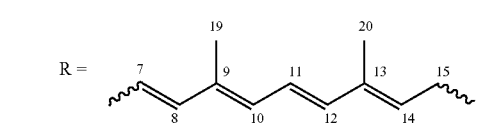

The oxygenated carotenoids (xanthophylls) most frequently include hydroxy, methoxy, carboxy, oxo, and epoxy functionality. Important and characteristic carotenoids (Compounds III through X) are lycopene (gamma, gamma-carotene) (I), beta-carotene (beta, beta-carotene) (III), alpha-carotene ((6'R)-beta, epsilon-carotene) (IV), beta-cryptoxanthin ((3R)-beta,beta-caroten-3-ol) (V), zeaxanthin ((3R, 3'R)-beta, beta carotene-3,3'-diol) (VI), lutein ("xanthophyll", (3R,3'R,6'R)-beta, epsilon-carotene-3,3'-diol) (VII), neoxanthin ((3S,5R,6R,3'S,5R,6'S)-5',6-epoxy-6,7-didehydro-5,6,S',6'-tetrahydro-beta,beta-carotene-3,5,3'-triol) (VIII), violaxanthin ((3S,5R,6R,3'S,5'R,6'S)-5,6,5',6'-diepoxy-5,6,5',6'-tetrahydro-beta,beta-carotene-3,3'-diol) (IX), fucoxanthin ((3S,5R,6S,3'S,5R,6'R)-5,6-epoxy-3,3',5'-trihydroxy-6',7'-didehydro-5,6,7,8,5',6'-hexahydro-beta, beta-caroten-8-one 3'-acetate) (X), canthaxanthin (beta,beta-carotene-4,4'-dione) (XI), astaxanthin ((3S,3'S)-3,3'-dihydroxy-beta,beta-carotene-4,4'-dione) beta-apo-8'-carotenal (8'-apo-beta-caroten-8'-al) (XIII) and peridinin ((3S,5R,6R,3'S,5'R,6'R)-epoxy-3,5,3'-trihydroxy-6,7-didehydro-5,6,5',6'-tetrahydro-10,11,20-trinor-beta,beta-caroten-19',11'-olide 3-acetate) (XIV).

III

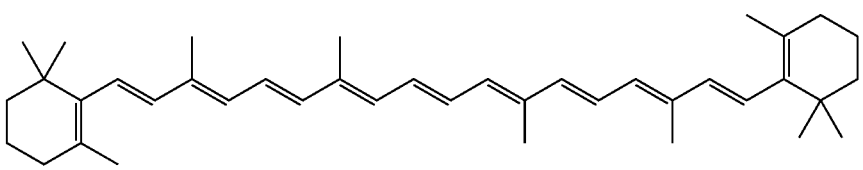

IV

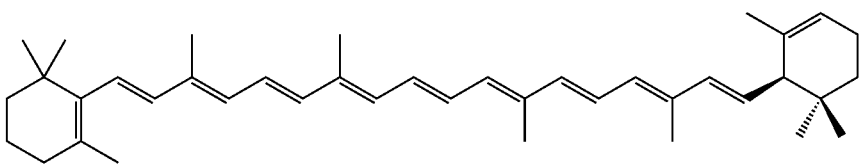

V

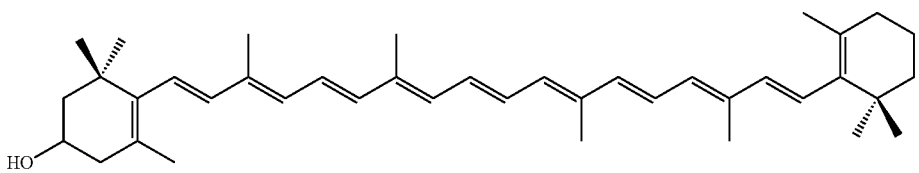

-continued
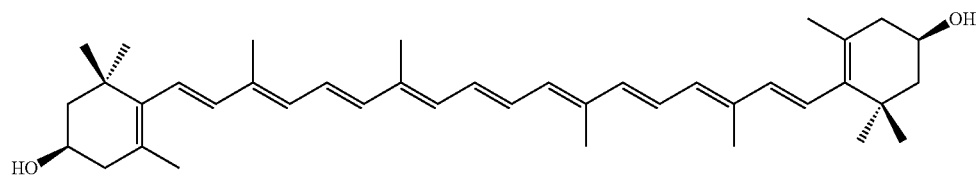
VI
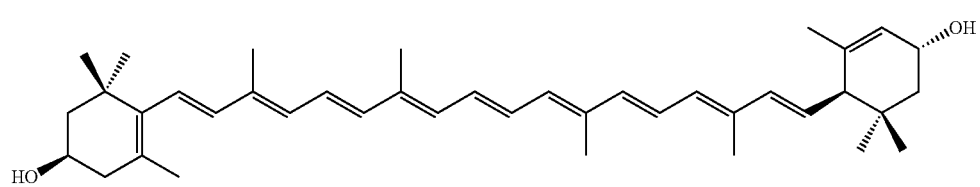
VII
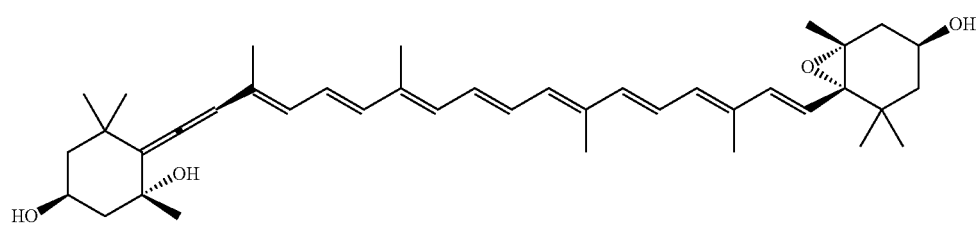
VIII
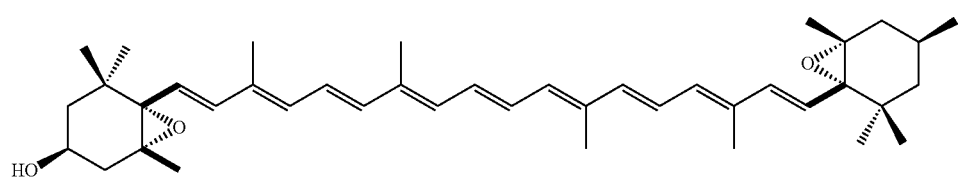
IX
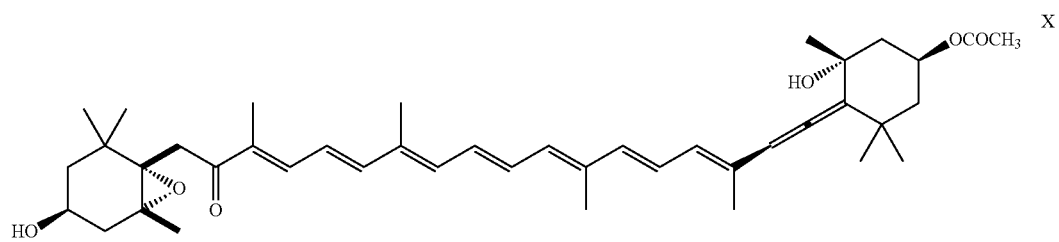
X
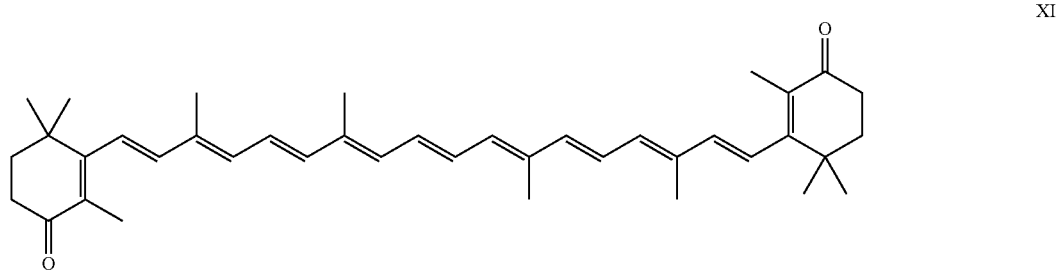
XI
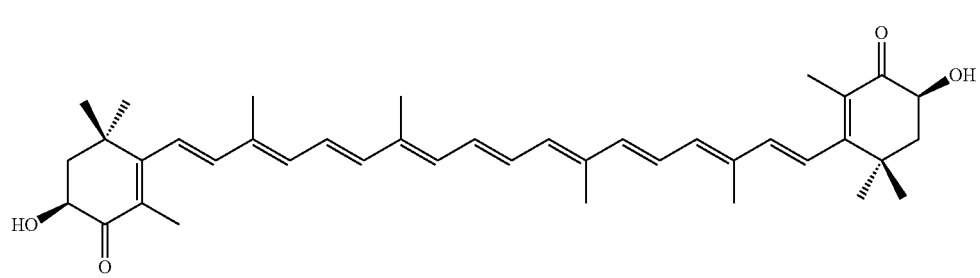
XII -continued

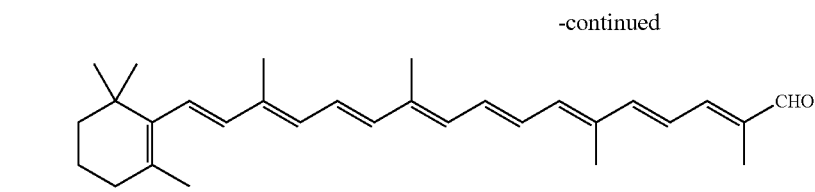

XIII

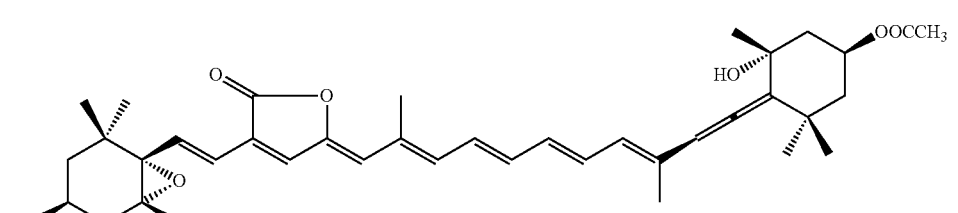

XIV

Normally carotenoids occur in Nature as the (all-E)-isomer. Some carotenoids undergo isomerization very easily during processing. For processing, it must be kept in mind that (E/Z)-isomerization can occur when a carotenoid is kept in solution. Normally the percentage of the (Z)-isomers is rather low, but it is enhanced at higher temperatures.

Humans and animals cannot synthesize xanthophylls like lutein and zeaxanthin, and the source of this has to be from diet. The occurrence of lutein and zeaxanthin in the macula has specific functions, viz., protection of the cells and tissues from ultra-violet light and reduced cataract risk. Lutein and zeaxanthin are known to comprise the macular pigment and lutein isomerizes into zeaxanthin in the macula.

There is evidence suggesting that lutein may have a protective effect against cancers of the breast, colon, lung, skin, cervix and ovaries and could bear promise in treatment of cardiovascular disease. Therefore, providing lutein to an individual for use in their diet or as nutritional supplements supports better human health and healthy vision.

Therefore, there is a high demand for xanthophyll crystals containing high amounts of trans (E)-lutein and/or zeaxanthin for its use as antioxidants, prevention of cataract and macular degeneration, as lung cancer-preventive agents, as agents for the absorption of harmful ultra-violet light from the rays of the sun and quencher of photo-induced free radical and reactive oxygen species, etc. Consequently, there is a need for providing or increasing the amount of carotenoids, such as xanthophylls, in blood plasma and tissues of humans.

Epi-lutein ((3R,3'S,6'R)-lutein), also known as 3'-epi-lutein, is formed by the epimerization of the 3' hydroxyl from an R configuration to no S configuration. Epi-lutein occurs in nature but only in very minute/trace amounts in very few plants, such as *Caltha palustris*, several roses and peonies as well as a metabolite of lutein in the human body. Therefore, less than about 1 mg/l gram of epi-lutein is present in a naturally occurring state of a plant material, more particularly less than about 0.1 mg/gram and most particularly less than about 0.01 mg/gram.

Epi-lutein analogs are also included as alternative materials suitable for use as described herein with carotenoids, such as xanthophylls. Such analogs include esters, amides, ethers, silyl ethers, carbonates, carbamates, sulfonates, phosphates, sulfoxides and the like of the hydroxyl groups present in epi-lutein. For example, a group of atoms that, when attached to a reactive functional group in a molecule, mask, reduce or prevent the reactivity of the functional group. Typically, the group may be selectively removed under appropriate conditions. Examples of suitable groups can be found in Greene and Wuts, Protective Groups in Organic Chemistry, 3.sup.rd Ed., 1999, John Wiley & Sons, NY and Harrison et al., Compendium of Synthetic Organic Methods, Vols. 1-8, 1971-1996, John Wiley & Sons, NY. Representative hydroxyl derivatizations include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPPS groups), glycol ethers, such as ethylene glycol and propylene glycol derivatives and allyl ethers.

It has been surprisingly found that the combination epi-lutein with a carotenoid, such as a xanthophyll lutein, zeaxanthin, β,β-carotene, violaxanthin, neoxanthin, astaxanthin, lycopene, canthaxanthin, capsanthin, capsorubin, derivatives thereof including esters, or mixtures thereof), increases the plasma uptake of the carotenoid, e.g, a xanthophyll such as lutein and/or zeaxanthin. Not to be limited by theory, it is possible that the epi-lutein helps to slow or prevent degradation of the carotenoid so that more of the carotenoid remains in the blood plasma. Consequently, an increased amount of the carotenoid then can be effectively delivered to the macula to help support the health of the tissue as well as treat or prevent possible AMD. Suitable epi-lutein material can be prepared by known methods and those as noted in the Examples contained herein.

The term "xanthophyll ester" is intended to include the mono or di-esters of "free" xanthophylls and, generally, at least one fatty acid. Typically the plant source contains the xanthophyll in the esterified form as a mono- or di-C12-C18 long chain, fatty acid such as lauric, myristic, oleic, linolenic and/or palmitic acids. Lutein in marigold flowers, zeaxanthin in wolfberries and capsanthin and capsorubin in pepper plants are present as xanthophyll diesters. The free or non-esterified xanthophyll can be found in other plants such as spinach, broccoli, kale and corn.

The term "free xanthophyll" (or free lutein, etc.) is intended to mean the carotenoid having a hydroxyl portion that remains after hydrolysis of the xanthophyll ester.

The purity of the carotenoid content utilized in the present invention is generally at least 90%, more particularly 95%, and even more particularly 99% or better, e.g., 99.5%.

The purified xanthophylls of the present invention can be utilized in the treatment of a diseases or conditions noted throughout this specification. They can also be used generally as nutritional supplements.

Typically the xanthophylls can be purified. For example, ultrafiltration can be used to remove unwanted components by molecular weight cut offs. The retentate from the filtration can be stored as a liquid or, for example, can then be further concentrated into a powder by spray drying, freeze drying, flash drying, fluidized bed drying, ring drying, tray drying, vacuum drying, radio frequency drying or microwave drying. Ultimately, the product should contain at least 95% by weight xanthophyll content, in particular about 99%, more particularly 99.5% or better.

The xanthophylls can be further purified by one or more methods known in the art, such as chromatography, gel chromatography, high performance liquid chromatography, crystallization, affinity chromatography, partition chromatography and the like. Identification of the particular xanthophylls can be accomplished by methods know to those skilled in the art and include $^1$H NMR, chemical degradation, chromatography and spectroscopy, especially homo- and heteronuclear two-dimensional NMR techniques for the characterization of the isolated isoprenoid compounds.

The term "purified" or "isolated" is used in reference to the purification and/or isolation of one or more xanthophylls as described above. Again using conventional methods known in the art, various xanthophylls can be separated into purified materials. In one aspect of the invention, the xanthophylls are substantially purified and isolated by techniques known in the art. The purity of the purified compounds is generally at least about 90%, preferably at least about 95%, and most preferably at least about 99% and even more preferably at least about 99.9% (e.g. about 100%) by weight.

Therefore, the present invention further provides bioavailable isolated xanthophylls described herein in combination with epi-lutein that are useful to treat various afflictions noted herein. The xanthophyll(s) and epi-lutein can be administered by a number of methods, as discussed infra.

The xanthophyll(s) and epi-lutein compositions of the invention can be incorporated into various foods, drinks, snacks, etc. In one aspect, the composition can be sprinkled onto a food product, prior to consumption. If sprinkled onto a food product, a suitable carrier such as starch, sucrose or lactose, can be used to help distribute the concentration of the xanthophyll(s) and epi-lutein making it easier to apply to the food product.

The xanthophyll(s) and epi-lutein compositions of the present invention can also be provided as supplements in various prepared food products. For the purposes of this application, prepared food product means any natural, processed, diet or non-diet food product to which a composition of the invention has been added. The xanthophyll(s) and epi-lutein compositions of the present invention can be directly incorporated into many prepared diet food products, including, but not limited to diet drinks, diet bars and prepared frozen meals. Furthermore, the xanthophyll(s) and epi-lutein compositions of the inventions can be incorporated into many prepared non-diet products, including, but not limited to candy, snack products such as chips, prepared meat products, milk, cheese, yogurt, sport bars, sport drinks, mayonnaise, salad dressing, bread and any other fat or oil containing foods. As used herein, the term "food product" refers to any substance fit for human or animal consumption.

The xanthophyll(s) and epi-lutein compositions of the invention can be added to various drinks, such as fruit juices, milkshakes, milk, etc.

The preferred method of administration is oral. The xanthophyll(s) and epi-lutein compositions of the invention can be formulated with suitable carriers such as starch, sucrose or lactose in tablets, capsules, solutions, syrups and emulsions. The tablet or capsule of the present invention can be coated with an enteric coating that dissolves at a pH of about 6.0 to 7.0. A suitable enteric coating, which dissolves in the small intestine but not in the stomach, is cellulose acetate phthalate.

Formulation of the xanthophyll(s) and epi-lutein compositions of the invention into a soft gel capsule can be accomplished by many methods known in the art. Often the formulation will include an acceptable carrier, such as an oil, or other suspending or emulsifying agent.

Suitable optional carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, wheat germ oil, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof in particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are also considered to be nutraceuticals. The term "nutraceutical" is recognized in the art and is intended to describe specific chemical compounds found in foods that can prevent disease or ameliorate an undesirable condition.

The formulations of the invention can further include various ingredients to help stabilize, or help promote the bioavailability of the components of the beneficial xanthophyll(s) and epi-lutein compositions of the invention or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals can be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Various additives can be incorporated into the present xanthophyll(s) and epi-lutein compositions. Optional additives of the present xanthophyll(s) and epi-lutein composition include, without limitation, hyaluronic acid, phospholipids, starches, sugars, fats, antioxidants, amino acids, proteins, flavorings, coloring agents, hydrolyzed starch(es) and derivatives thereof or combinations thereof.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

Compositions comprising the xanthophyll(s) and epi-lutein of the invention can be manufactured by methods of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the xanthophyll epi-lutein compositions into preparations that can be used.

The xanthophyll(s) and epi-lutein compositions of the invention can take a form suitable for virtually any mode of administration, including, for example, oral, buccal, systemic, injection, transdermal, rectal, vaginal, etc., or a form suitable for administration by inhalation or insufflation.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the xanthophyll(s) and epi-lutein compositions in aqueous or oily vehicles. The xanthophyll(s) and epi-lutein compositions can also contain formulating agents, such as suspending, stabilizing and/or dispersing agent. The formulations for injection can be presented in unit dosage form, e.g., in ampoules or in multidose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the xanthophyll and epi-lutein compositions can be dried by any art-known technique, such as lyophilization, and reconstituted prior to use.

For transmucosal administration, penetrants appropriate to the barrier to be permeated are used in the formulation. Such penetrants are known in the art.

For oral administration, the xanthophyll(s) and epi-lutein compositions of the invention can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants potato starch or sodium starch glycolate); or wetting agents (e.g., sodium lauryl sulfate). The tablets can be coated by methods well known in the art with for example, sugars, films or enteric coatings.

Liquid preparations thr oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Preparations for oral administration can be suitably formulated to give controlled release of the xanthophyll(s) and epi-lutein composition as is well known.

For buccal administration, the xanthophyll(s) and epi-lutein compositions can take the form of tablets or lozenges formulated in conventional manner.

For rectal and vaginal routes of administration, the xanthophyll(s) and epi-lutein compositions can be formulated as solutions (for retention enemas) suppositories or ointments containing conventional suppository bases such as cocoa butter or other glycerides.

For nasal administration or administration by inhalation or insufflation, the xanthophyll(s) and epi-lutein compositions can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the xanthophyll(s) and epi-lutein compositions can be formulated as a depot preparation for administration by implantation or intramuscular injection. The xanthophyll(s) and epi-lutein compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the xanthophyll(s) and epi-lutein compositions for percutaneous absorption, can be used. To this end, permeation enhancers can be used to facilitate transdermal penetration of the compositions. Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other delivery systems can be employed. Liposomes and emulsions are well-known examples of delivery vehicles that can be used to deliver xanthophyll(s) and epi-lutein compositions. Certain organic solvents such as dimethylsulfoxide (DMSO) can also be employed, although usually at the cost of greater toxicity.

The xanthophyll(s) and epi-lutein compositions disclosed herein can, if desired, be presented in a pack or dispenser device, which can contain one or more unit dosage forms containing the xanthophyll(s) and epi-lutein compositions. The pack can, for example, comprise metal or plastic foil, such as a blister pack. The pack or dispenser device can be accompanied by instructions for administration.

Soft gel or soft gelatin capsules can be prepared, for example, without limitation, by dispersing the formulation in an appropriate vehicle (e.g., rice bran oil, and/or beeswax) to form a high viscosity mixture. This mixture is then encapsulated with a gelatin based film using technology and machinery known to those in the soft gel industry. The capsules so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally a carrier such as rice bran oil or wheat germ oil and/or beeswax if desired) and can include, apart from the xanthophylls, a hydrophilic matrix. The hydrophilic matrix, if present, is a polyethylene glycol having an average molecular weight of from about 200 to 1000. Further ingredients are optionally thickening agents and/or emulsifying agent(s). In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes is mature technologies and is all widely available to any one wishing to prepare soft gelatin capsules.

Emulsifying agents can be used to help solubilize the ingredients within the soft gelatin capsule. Specific examples of the surfactant, emulsifier, or effervescent agent include D-sorbitol, ethanol, carrageenan, carboxyvinyl polymer, carmellose sodium, guar gum, glycerol, glycerol fatty acid ester, cholesterol, white beeswax, dioctyl sodium sulfosuccinate, sucrose fatty acid ester, stearyl alcohol, stearic acid, polyoxyl 40 stearate, sorbitan sesquioleate, cetanol, gelatin, sorbitan fatty acid ester, talc, sorbitan trioleate, paraffin, potato starch, hydroxypropyl cellulose, propylene glycol, propylene glycol fatty acid ester, pectin, polyoxyethylene (105) polyoxypropylene (5) glycol, polyoxyethylene (160) polyoxypropylene (30) glycol, polyoxyethylene hydrogenated castor oil, polyoxyethylene hydrogenated castor oil 40, polyoxyethylene hydrogenated castor oil 60, polyoxyl 35 castor oil, polysorbate 20, polysorbate 60, polysorbate 80, macrogol 400, octyldodecyl myristate, methyl cellulose, sorbitan monooleate, glycerol monostearate, sorbitan monopalmitate, sorbitan monolaurate, dimethylamine oxide solution, sodium lauryl sulfate, lauromacrogol, dry sodium carbonate, tartaric acid, sodium hydroxide, purified soybean lecithin, soybean lecithin, potassium carbonate, sodium hydrogen carbonate, medium-chain triglyceride, citric anhydride, cotton seed oil-soybean oil mixture, and liquid paraffin.

The present invention also provides packaged formulations of the xanthophyll(s) and epi-lutein compositions disclosed herein and instructions for use of the product for appropriate condition s). Typically, the packaged formulation, in whatever form, is administered to an individual in need thereof. Typically, the dosage requirement is between about 1 to about 4 dosages a day.

Although the present invention describes the preparation, use, manufacture and packaging of the xanthophyll(s) and epi-lutein compositions disclosed herein in soft gelatin capsules for treatment of various conditions, it should not be considered limited to only soft gelatin capsules. Ingestible xanthophyll(s) and epi-lutein compositions disclosed herein can be delivered in traditional tablets, pills, lozenges, elixirs, emulsions, hard capsules, liquids, suspensions, etc. as described above.

The xanthophyll(s) and epi-lutein compositions disclosed herein will generally be used in an amount effective to achieve the intended result, for example in an amount effective to treat or prevent the particular related condition being treated. The composition can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a xanthophyll(s) and epi-lutein composition to a patient suffering from pain provides therapeutic benefit not only when the underlying condition is eradicated or ameliorated, but also when the patient reports a decrease in the severity or duration of the physical discomfort associated with the pain.

For prophylactic administration, the xanthophyll(s) and epi-lutein composition can be administered to a patient at risk of developing one of the previously described conditions.

The amount of xanthophyll(s) and epi-lutein composition administered will depend upon a variety of factors, including, for example, the particular indication being treated, the mode of administration, whether the desired benefit is prophylactic or therapeutic, the severity of the indication being treated and the age and weight of the patient, etc. Determination of an effective dosage is well within the capabilities of those skilled in the art.

Total dosage amounts of a xanthophylls) and epi-lutein composition will typically be in the range of from about 0.0001 or 0.001 or 0.01 mg/kg/day to about 100 mg/kg/day, but may be higher or lower, depending upon, among other factors, the activity of the components, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. Skilled artisans will be able to optimize effective local dosages without undue experimentation.

The following paragraphs enumerated consecutively from 1 through 14 provide for various aspects of the present invention. In one embodiment, in a first paragraph (1), the present invention provides a composition comprising:

epi-lutein in an amount greater than a naturally occurring amount present in a carotenoid material and a carotenoid or derivative thereof, including esters thereof.

2. The composition of paragraph 1, wherein the carotenoid is lutein, zeaxanthin, β,β-carotene, violaxanthin, neoxanthin, astaxanthin, lycopene, canthaxanthin, capsanthin, capsorubin, derivatives thereof including esters, or mixtures thereof.

3. A composition comprising:

from about 5 to about 95 weight percent epi-lutein and from about 95 to about 5 weight percent of a carotenoid, wherein the weight percentages equal 100 weight percent.

4. The composition of paragraph 3, wherein the carotenoid is lutein, zeaxanthin, β,β-carotene, violaxanthin, neoxanthin, astaxanthin, lycopene, canthaxanthin, capsanthin, capsorubin, derivatives thereof including esters, or mixtures thereof.

5. A method to increase the uptake of a carotenoid in a subject's plasma comprising the step of providing any of the compositions of paragraphs 1 through 4 to a subject.

6. A method of therapy or prevention of age-related macular degeneration in a human subject by increasing deposition of yellow macular pigment in the macula of an eye of the subject, the method comprising orally administering to the subject a sufficient amount of epi-lutein to increase the serum concentration of carotenoid(s) in the subject to at least 0.5 μg/ml and maintain the increased serum carotenoid concentration at or above 0.5 μg/ml for at least 14 days, and at least until the macular concentration of carotenoid(s) has achieved equilibrium.

7. The method as in paragraph 6, wherein the daily dose of epi-lutein is at least 0.1 mg per day.

8. The method as in paragraph 7, wherein the daily dose of epi-lutein is at least about 1.0 mg per day.

9. The method as in paragraph 8, wherein said daily dose of epi-lutein is about 0.017 mg/kg body weight.

10. The method to increase the concentration of carotenoids in a subject's plasma, the method comprising orally administering to the subject a sufficient amount of epi-lutein to increase the serum concentration of carotenoid(s) in the subject's plasma to at least 0.1 μg/ml.

11. The method of paragraph 9, wherein the increased serum carotenoid concentration is maintained at or above 0.1 μg/ml for at least 14 days.

12. The method as in paragraph 10, wherein the daily dose of epi-lutein is from 0.1 to 50 mg per day.

13. The method as in paragraph 10, wherein the daily dose of epi-lutein is at least about 1.0 mg per day.

14. A method as in paragraph 6, wherein said daily dose of epi-lutein is about 0.017 mg/kg body weight.

It should be understood that throughout the specification, one or more of the components noted herein can be excluded from a given composition.

The following examples are not to be meant as limiting but are presented to provide additional information and support for the invention.

EXAMPLES

Example 1

Study Design:
14 days wash-out period before this study
Subject: 3 wistar rats each group
Feeding type: intravenous administration
Feeding Dosage:
Group A: 4 mg lutein/Kg body weight
Group B: (2 mg lutein+2 mg epi-lutein)/Kg body weight
Group C: 4 mg zeaxanthin/Kg body weight
Group D: (2 mg zeaxanthin 2 mg epi-lutein)/Kg body weight
Blood sampling: 15, 30, 60 minutes, 3 and 6 hours after feeding
Results:

FIG. 1 shows the degradation of lutein with/without epi-lutein. Line B is lutein with epi-lutein and line A is lutein without epi-lutein.

Figure 2:
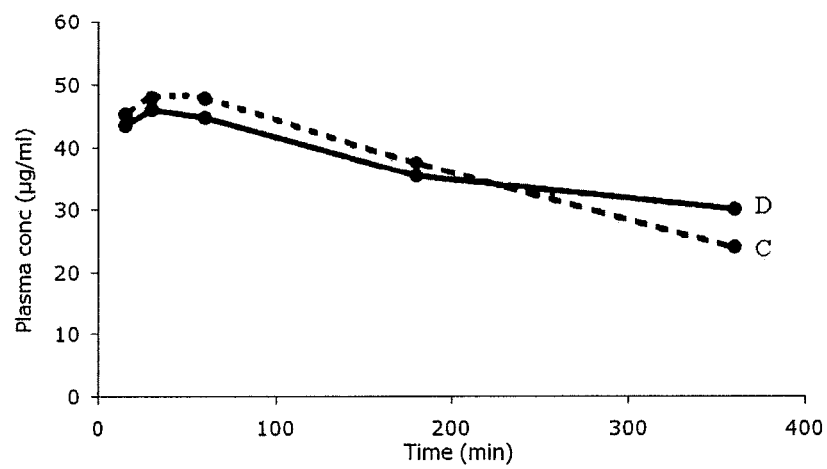
FIG. 2 shows the degradation of zeaxanthin with/without epi-lutein.

FIG. 2 shows the degradation of zeaxanthin with/without epi-lutein. Line D is zeaxanthin with epi-lutein and line C is zeaxanthin without epi-lutein.

Table 1 provided below details pharmacokinetic characteristics of lutein and zeaxanthin with/without epi-lutein.

TABLE 1

| | Group | | | |
|---|---|---|---|---|
| | A | B | C | D |
| $AUC_{0-t}$ (μg × h/mL) | 11669 | 12630 | 12827 | 12760 |
| $T^{1/2}$ (min) | 305 | 481 | 300 | 541 |
| $AUC_{0-inf}$ (μg × h/mL) | 21301 | 32394 | 23255 | 36348 |

The data indicated that the plasma half life of Lutein and Zeaxanthin was substantially prolonged after treatment with epi-lutein.

Preparation of Epi-Lutein:

With nitrogen protection, 50 g powder of free form lutein (commercial, UV=80%) and 2.5 L THF were mixed with stirring in a flask until the lutein was fully dissolved. 1.0 L $H_2SO_4$ (2N) was slowly added to the solution, and the temperature of reaction mixture was maintained between about 25° C. and about 30° C. After addition of $H_2SO_4$ (2N), the reaction mixture was stirred between 25° C. and about 30° C. thr 16 hours.

The resulting mixture was filtered and the filtrate was neutralized with 3.3 L $NaHCO_3$ (5%). 1.0 L dichloromethane was added to the neutralized solution, and the mixture was stirred for 10 min. The solution was allowed to separate into layers. After separation, the organic phase was washed with 1.0 L deionized water, followed by drying with anhydrous sodium sulfate.

After filtration, the filtrate was concentrated under reduced pressure to provide a solid. Vacuum drying afforded 48 g of dark red solid. The solid was added to 2.4 L ethanol (95%) and the mixture was stirred for 30 min. The resulting mixture was filtered. 22.5 g dark red solid was produced after removal of solvent and vacuum drying of the filtrate. Content of epi-lutein was approximately 48.7% by weight. The material can be further purified as noted in U.S. Pat. No. 6,420,614. Additionally, epi-lutein can be purchased from Wako Pure Chemical Industries, Ltd. (98% purity).

HPLC Conditions

HPLC: Shimdazu 20AT series with UV detection and autosample

Mobile phase: A, hexane: B, ethyl acetate=75:25
Column: Prevail silica (1.00 mm*4.0 mm, 3 μm)
Temperature: 30° C.
UV-detection: 450 nm.
Flow rate: 1 mL/min
Concentration: 0.5 mg/ml in mobile phase
Injection volume: 10 ul UV Conditions The optimum sample quantity was about 15 mg. The sample was weighed accurately in a 50 ml volumetric flask and the quantity was noted as W.

The sample was dissolved in 20 ml of THF. The volume was brought to 50 ml with ethanol.

0.2 ml of the THF-ethanol solution was diluted with 25 ml ethanol.

The solution was mixed well and added to a quartz cell for UV measurement using ethanol for as a reference sample.

The optimal wavelength was 446 nm. The absorption A was recorded.

Calculation:

UV %=(dilution factor*$A_{446}$)/255/$W$*100%

Where 255 ml/mg is the extinction coefficient.

Results:

Total carotenoids amount (UV %): 68.6%

|  | Area % (HPLC) | Content % |
| --- | --- | --- |
| Lutein | 13.6 | 9.3 |
| Zeaxanthin | 0.7 | 0.5 |
| 3'-epi-lutein | 71.0 | 48.7 |

| Peak# | Ret. Time | Area | Height | Area % |
| --- | --- | --- | --- | --- |
| 1 | 5.134 | 193521 | 16028 | 6.551 |
| 2 | 10.21 | 55956 | 1566 | 1.8942 |
| 3 | 12.575 | 4657 | 240 | 0.1577 |
| 4 | 17.15 | 5622 | 194 | 0.1903 |
| 5 | 17.978 | 107364 | 2664 | 3.6345 |
| 6 | 19.162 | 401900 | 11199 | 13.605 |
| 7 | 21.888 | 19889 | 713 | 0.6733 |
| 8 | 24.249 | 2100104 | 48288 | 71.0921 |
| 9 | 29.646 | 56562 | 1146 | 1.9147 |
| 10 | 33.273 | 7414 | 187 | 0.251 |
| 11 | 52.792 | 1072 | 62 | 0.0363 |

Peak 6=lutein
Peak 7=zeaxanthin
Peak 8=epilutein

Figure 3:
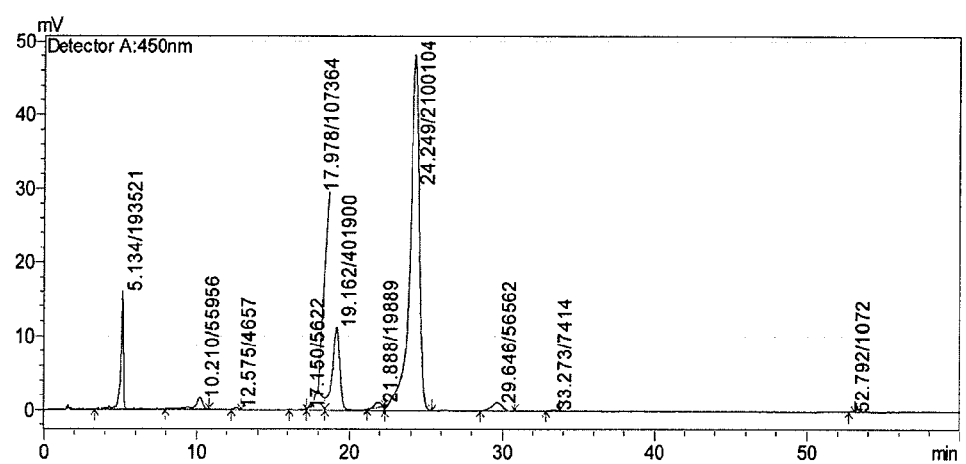
FIG. 3 is an HPLC chromatogram of isolated epi-lutein prepared in this application.

See FIG. 3 for an HPLC chromatogram.

Results Epi-Lutein Study

Test system (laboratory animals)

| Species and strain: | Rats, Sprague-Dawley |
| --- | --- |
| Supplier: | Institut für Labortierkunde und Genetik Universität Wien/Medizinische Fakultät Brauhausgasse 34 2325 Himberg Tel. Nr.: 02235/867250 Fax Nr.: 02235/86053 |
| Number and sex of animals to be received: | 5 male animals |
| Body weight range at administration: | Approximately 200 g |
| Range of the body weights: | At the start of the study a maximum deviation of 20% of any individual body weight from the mean of the sex concerned was accepted. |

Justification for the Dose Selection

Based on published studies in rats and mice the dose levels chosen are considered safe for the animals and will likely yield plasma levels above the Limit of Quantification (LOQ).

Justification of the Species

The rat is a common standard rodent species for pharmacology and toxicity studies as well as for pharmacokinetic studies.

| Animal maintenance Hygiene | Optimal hygienic conditions. |
| --- | --- |
| Animal room | Standard |
| Room temperature | About 22° C. ± 2° C. |
| Relative humidity | About 30%-70%. |
| Light | 12 hours light, 12 hours dark, only artificial light from 6 a.m. to 6 p.m. |
| Cages | Makrolon cages type III (39 cm × 23 cm bottom area, 18 cm height) with wire mesh lids, single caging. |
| Food | Ssniff maintenance diet for mice and rats R/M-H V-1534-300, ad libitum. |
| Water | Tap water, from Macrolon-bottles with stainless steel cannulae or from a watering system, ad libitum. |
| Bedding material | Aspen wood chips, supplied by ABEDD Dominik Mayr KEG, A-8580 Köflach, autoclaved. Random samples of the bedding material were analysed for contaminants by the supplier. Changes once a week. |
| Environmental Enrichment | Nibbling wood bricks (10 cm × 2 cm × 2 cm) and nesting material, both from the same material and source as the bedding material, were offered to the animals once a week. |
| Acclimatisation | At least 5 days. |
| Identification | Individual labelling with felt-tipped pen on the tail and cage labels. |
| Humane endpoints for animals suffering from severe distress or pain | Moribund animals and animals in severe distress or pain were removed when noticed, euthanised and necropsied. Criteria for clinical signs and conditions of animals requiring humane killing were derived from the "OECD Guidance Document on the recognition, assessment, and use of clinical signs as humane endpoints for experimental animals used in safety evaluation" (21 Dec. 2000). Decisions were be made by the Study director and/or an veterinarian. |

Study Design: Oral administration (gavage) of Treatment I for 7 consecutive days in 5 rats followed by a 14 days wash-out period and oral administration (gavage) of Treatment II for 7 consecutive days Blood Sampling: On day 7 of treatment prior to treatment and 15 min, 1, 3, 6, 9, 12 and 24 hours after treatment.

About 400 μL blood were be transferred to Vacutainer tubes containing EDTA. Whole blood samples were centrifuged, as soon as possible from the designated time of collection, at 1200 g for approximately 10 minutes.

All plasma samples (at least 200 μL) were be stored deep frozen at ≤−30° C., until shipping on dry ice.

Treatments:

|  | Treatment I (mg/kg BW) | Treatment II (mg/kg BW) |
| --- | --- | --- |
| Lutein | 0.282 | 0.147 |
| Epi-lutein | 0.000 | 0.135 |
| Zeaxanthin | 0.018 | 0.018 |
| Sum | 0.300 | 0.300 |

-continued

|  | Treatment I Lutein | Treatment II | | |
|---|---|---|---|---|
|  |  | Lutein | Epi-Lutein | Lutein + Epi-Lutein |
| $C_{max}$ (ng/ml) | 941 | 939 | 428 | 1244 |
| $AUC_{0-\tau}$ (ng × h × ml$^{-1}$) | 18149 | 14341 | 6286 | 20627 |
| $AUC_{0-12\,h}$ (ng × h × ml$^{-1}$) | 9783 | 9345 | 3724 | 13069 |

Plasma Analysis: Lutein, Epilutein, Zeaxanthin and Oxidized metabolites
Results:
The plasma levels of zeaxanthin in all samples were below limit of determination (<10 ng/ml).

Figure 4:
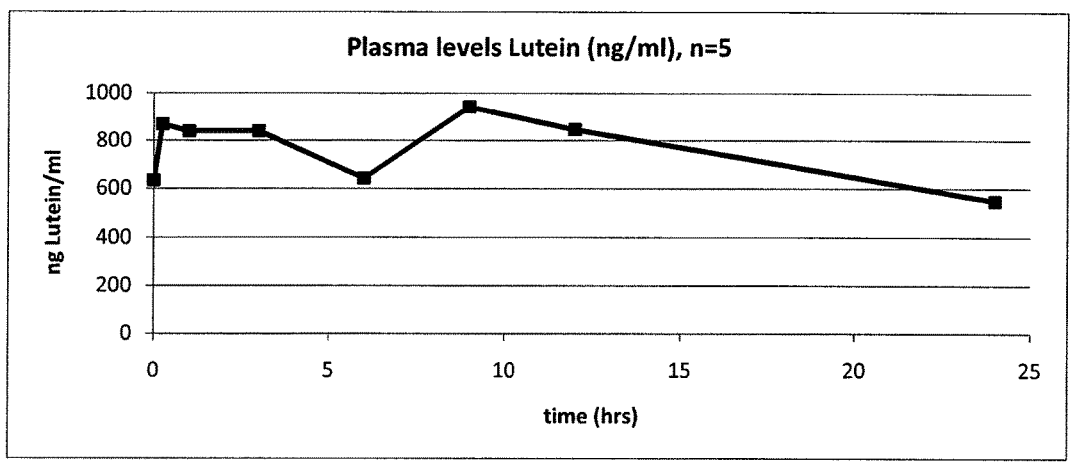
FIG. 4 provides plasma levels of lutein observed on day 7 after treatment I (n=5).
Figure 5:
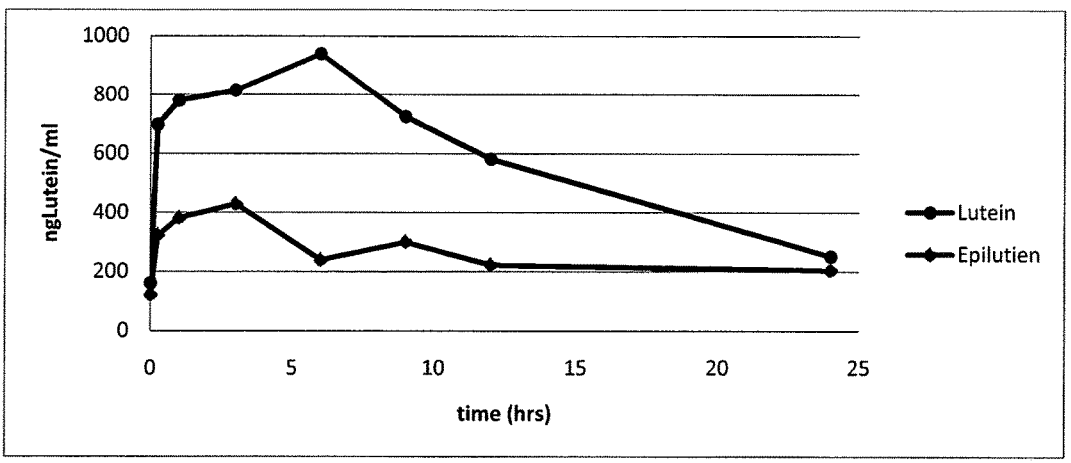
FIG. 5 provides plasma levels of lutein and epi-lutein observed on day 7 after Treatment I (n=5).

Note in FIG. 4 the plasma levels of lutein observed on day 7 of treatment I (corresponding to 0.282 mg lutein/kg BW) and on FIG. 5 the plasma levels of lutein and epi-lutein observed on day 7 of treatment II (corresponding to 0.147 mg lutein and 0.135 mg epi-lutein/kg BW).

Figure 6:
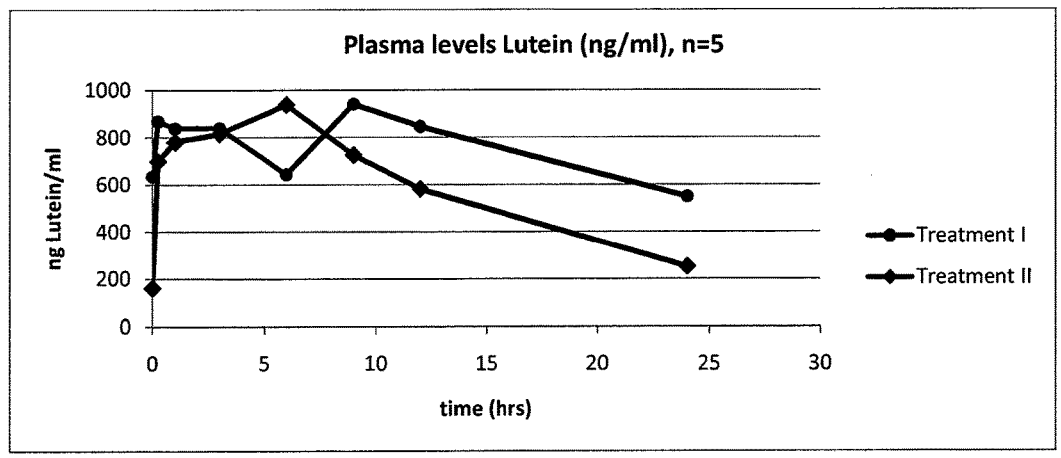
FIG. 6 provides comparative plasma levels of lutein observed after Treatment I and II, n=5.

FIG. 6 provides the plasma levels of lutein observed on day 7 of Treatment I or II, respectively. It should be emphasized that Treatment I and II consisted of 0.282 and 0.147 mg lutein/kg BW, respectively.

Figure 7:
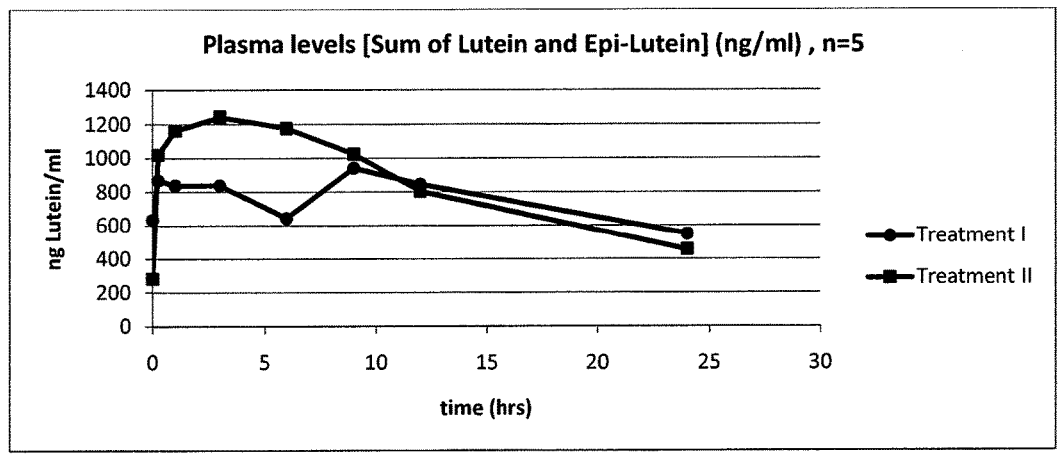
FIG. 7 are results of comparative plasma levels of lutein and the sum of lutein/epi-lutein after Treatment I and II, respectively.

FIG. 7 provides the plasma levels of lutein observed on day 7 after Treatment I and the sum plasma levels of lutein and epi-lutein observed on day 7 after Treatment II.
It should be emphasized that Treatment I consisted of 0.282 mg lutein/kg BW and Treatment II of 0.147 mg lutein+0.135 epi-lutein mg/kg BW.

Table 2 provides the main pharmacokinetic parameters observed fir lutein and epi-lutein based on a dosing interval ($\tau$) of 24 hours and for the first 12 hours after treatment (corresponding to the range with frequent blood sampling).

|  | Treatment I Lutein | Treatment II | | |
|---|---|---|---|---|
|  |  | Lutein | Epi-Lutein | Lutein + Epi-Lutein |
| $C_{max}$ (ng/ml) | 941 | 939 | 428 | 1244 |
| $AUC_{0-\tau}$ (ng × h × ml$^{-1}$) | 18149 | 14341 | 6286 | 20627 |
| $AUC_{0-12\,h}$ (ng × h × ml$^{-1}$) | 9783 | 9345 | 3724 | 13069 |

Figure 8:
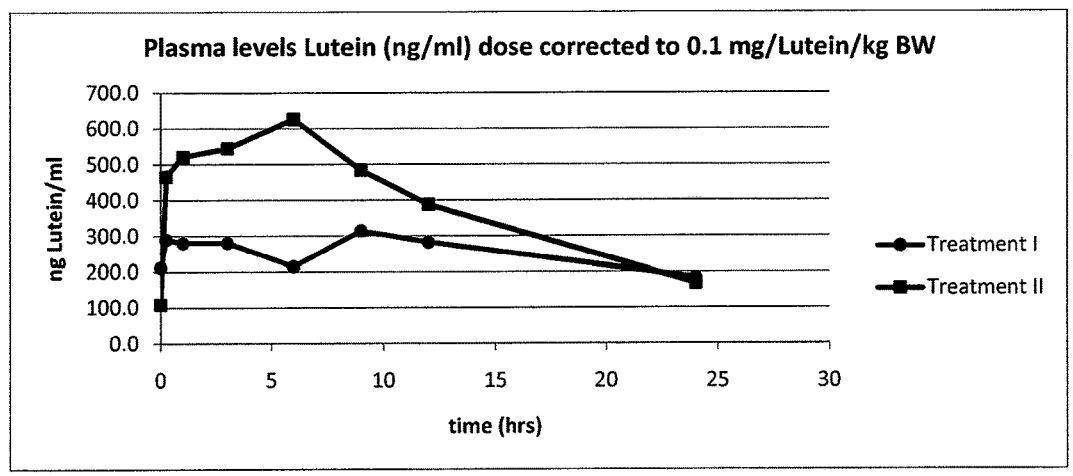
FIG. 8 provides plasma levels of lutein observed on day 7 of the corresponding treatment, corrected for a dose of 0.1 mg lutein/kg BW, n=5.

FIG. 8 provides the plasma levels of lutein observed after both treatments corrected for the dose and represent the plasma response to 0.1 mg lutein/kg BW.

Table 3 provides the pharmacokinetic parameters for lutein derived from a dose equivalent of 0.1 mg/kg BW administered either as pure compound (Treatment I) or as a mixture together with epi-lutein (Treatment II).

TABLE 3

Main pharmocokinetic parameters of Lutein (dose corrected to 0.1 mg Lutein/kg BW)

|  | Treatment I Lutein | Treatment II Lutein |
|---|---|---|
| $C_{max}$ ([ng/ml]/0.1 mg Lut/kg BW) | 314 | 626 |
| $AUC_{0-\tau}$ (ng × h × ml$^{-1}$/0.1 mg Lut/kg BW) | 6050 | 9560 |
| $AUC_{0-12\,h}$ (ng × h × ml$^{-1}$/ 0.1 mg Lut/kg BW) | 3261 | 6230 |

CONCLUSIONS

A mixture of Lutein/Epilutein (approximately 1:1 ratio) amounting to 0.3 mg/kg BW administered orally yields substantial higher plasma levels of lutein when compared to pure lutein at a dose of 0.3 mg/kg BW (FIG. 7).

Correspondingly, the pharmacokinetic parameters of lutein (Treatment I) compared to lutein and epi-lutein (Treatment II) derived from the plasma levels are increased by 14% (time interval 0-24 hours) or 33% (time interval 0-12 hours). The latter time range represents the sampling interval and is therefore considered more valid for this study (Table 3).

The peak concentration of lutein (Treatment I) as compared to lutein and epi-lutein (Treatment II) was shown to be increased by 32% (Table 2).

If the two treatments are corrected for the difference in the lutein content (i.e. to a plasma response against 0.1 mg lutein/kg BW either administered as single compound or mixed with approximately 0.1 mg epi-lutein/kg BW) the pronounced effect of epi-lutein on the plasma levels of lutein is clearly observed (FIG. 8). Based on the time interval 0-12 hours, representing the interval with frequent blood sampling, an increase in the pharmacokinetic parameters of about 100% was observed (Table 3).

Figure 9:
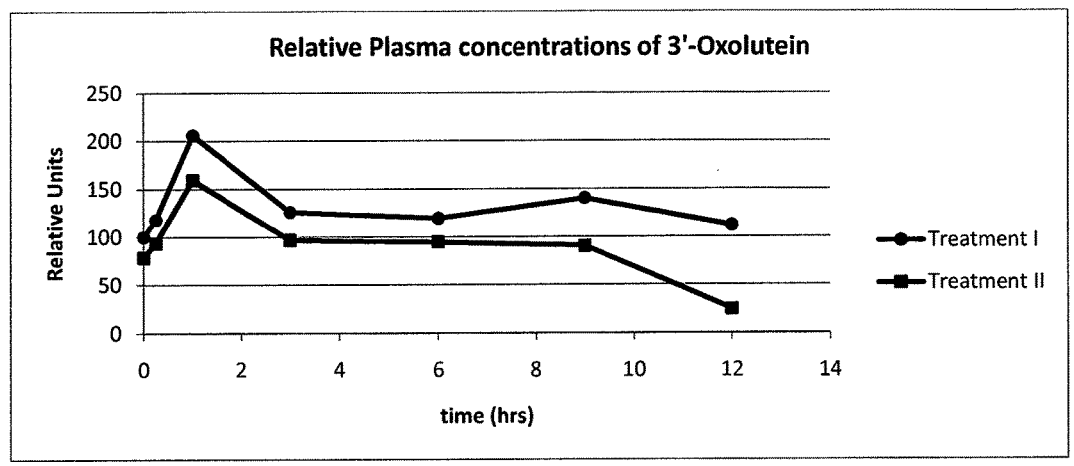
FIG. 9 provides Plasma levels of 3'-oxolutein observed on day 7 (relative comparison), n=5.
Figure 10:
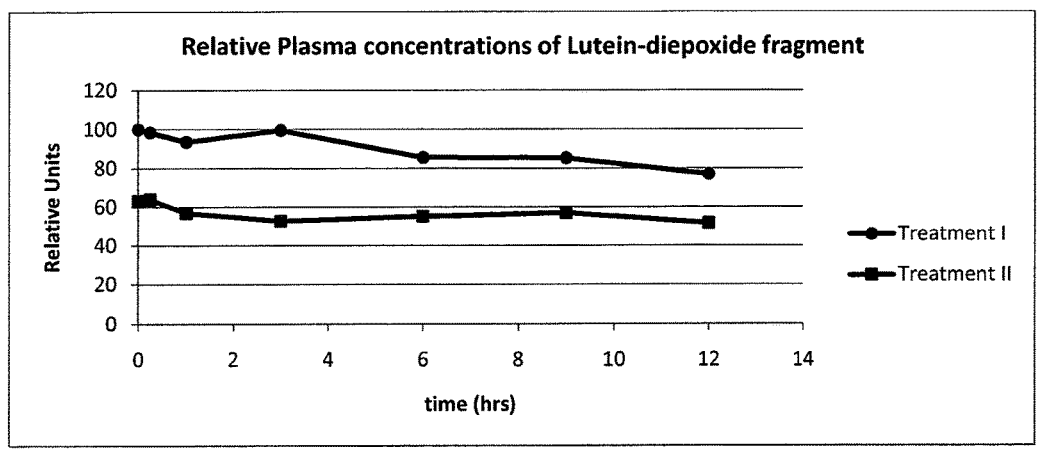
FIG. 10 provides Plasma levels of a lutein-diepoxide fragment (5,6-Epoxy-3-hydroxy-12'-β,ε-carotene-12'-al) observed on day 7 (relative comparison), n=5.

Analysis of Oxidized Metabolites:
FIGS. 9 and 10 provide the comparable plasma levels of 3'-oxolutein and a fragment typical for lutein-diepoxide, respectively.

The basal level observed predose to Treatment I was set to 100.

As seen in FIGS. 9 and 10, the amount of oxidized products of lutein observed in plasma after Treatment II are substantial lower than Treatment I. Less amount of oxidized metabolite after treatment II indicates that epi-lutein has an ability to keep the amount of lutein and epi-lutein (total xanthophylls) in a higher level in plasma or prevents oxidation of lutein/epi-lutein in plasma, which is highly advantageous to human physiology, e.g. eye health.

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method to increase the uptake of a carotenoid in a subject's plasma comprising the step of:
orally administering a composition to a subject, wherein the composition comprises from about 5 to about 95 weight percent of a purified epi-lutein or esters thereof component and from about 95 to about 5 weight percent of a purified carotenoid or esters thereof component, wherein the weight percentages of the purified epi-lutein or esters thereof component and the purified carotenoid or esters thereof component equal 100 weight percent of the combination.

2. The method of claim 1, wherein the composition further comprises lutein, zeaxanthin, β,β-carotene, violaxanthin, neoxanthin, astaxanthin, lycopene, canthaxanthin, capsanthin, capsorubin, including esters, or mixtures thereof.

3. The method of claim 1, wherein the composition treats age-related macular degeneration (AMD) in a human subject by increasing deposition of yellow macular pigment in the macula of an eye of the subject, comprising the step of orally administering to the subject a sufficient amount of epi-lutein to increase the serum concentration of carotenoid(s) in the subject to at least 0.5 µg/ml and maintain the increased serum carotenoid concentration at or above 0.5 µg/ml for at least 14 days, and at least until the macular concentration of carotenoid(s) has achieved equilibrium.

4. The method of claim 3, wherein the daily dose of epi-lutein is at least 0.1 mg per day.

5. The method of claim 4, wherein the daily dose of epi-lutein is at least about 1.0 mg per day.

6. The method of claim 3, wherein the daily dose of epi-lutein is about 0.017 mg/kg body weight.

7. The method of claim 1, wherein the composition is administered in the range of from 0.01 mg/kg/day to 100 mg/kg/day.

8. The method of claim 1, wherein the carotenoid is lutein.

* * * * *